United States Patent [19]
Comoglio

[11] Patent Number: 5,968,501
[45] Date of Patent: *Oct. 19, 1999

[54] HEPATOCYTE GROWTH FACTOR—INDUCED PROLIFERATION AND DIFFERENTIATION OF ERYTHROID CELLS

[75] Inventor: Paolo Comoglio, Turin, Italy

[73] Assignee: Dompé S.p.A., Italy

[ * ] Notice: This patent issued on a continued prosecution application filed under 37 CFR 1.53(d), and is subject to the twenty year patent term provisions of 35 U.S.C. 154(a)(2).

[21] Appl. No.: 08/836,896

[22] PCT Filed: Nov. 22, 1995

[86] PCT No.: PCT/EP95/04589

§ 371 Date: May 22, 1997

§ 102(e) Date: May 22, 1997

[87] PCT Pub. No.: WO96/15802

PCT Pub. Date: May 30, 1996

[30] Foreign Application Priority Data

Nov. 24, 1994 [IT] Italy .................... MI94A2382

[51] Int. Cl.$^6$ .................... A61K 38/18
[52] U.S. Cl. .............. 424/85.1; 435/69.4; 435/69.5; 435/198.1; 530/399
[58] Field of Search .............. 424/85.1; 435/69.1, 435/69.5, 325, 360, 365.1, 69.4, 198.1; 530/351, 399

[56] References Cited

U.S. PATENT DOCUMENTS

| | | | |
|---|---|---|---|
| 5,004,805 | 4/1991 | Gohda et al. | 530/399 |
| 5,328,836 | 7/1994 | Shima et al. | 435/69.4 |
| 5,328,837 | 7/1994 | Godowski et al. | 530/399 |
| 5,459,069 | 10/1995 | Palsson et al. | |
| 5,599,703 | 2/1997 | Davis et al. | 435/373 |

FOREIGN PATENT DOCUMENTS

| | | |
|---|---|---|
| 0 461 560 | 12/1991 | European Pat. Off. |
| 0 550 769 | 7/1993 | European Pat. Off. |
| 93 15754 | 8/1993 | WIPO |

OTHER PUBLICATIONS

Biochemical and Biophisical Research Communications, vol. 194, No. 1 (Jul. 15, 1993), pp. 178–186, K. Mizuno et al, "Hepatocyte Growth Factor Stimulates Growth of Hematopoietic Progenitor Cells".

Experimental Hematology, vol. 22, No. 8 (Aug. 1994), p. 814, XP 000564570, S. Aizawa et al, "Effects of Hepatocyte Growth Factor on Hemopoietic Cells in Human Long–Term Bone Marrow Culture".

Flood, vol. 80 (Nov. 15, 1992), pp. 2454–2457, T. Kmiecik et al, "Hepatocyte Growth Factor is a Synergistic Factor for the Growth of Hematopoietic Progenitor Cells".

Cytokine, vol. 6, No. 3 (May 1994), pp. 285–294, XP 000564568, S. Nakamura et al, "Production of Hepatocype Growth Factor by Human Haematopoietic Cell Lines".

The Journal of Cell Biology, vol. 127, No. 6, Part 1 (Dec. 1994), pp. 1743–1754, XP 000564573, Galimi et al, "Hepatocyte Growth Factor Induces Proliferation and Differentiation of Multipotent etc.".

Blood, vol. 85, No. 11 (Jun. 1, 1995), pp. 3093–3100, XP 000564571, T. Nishino et al, "Hepatocyte Growth Factor as a Hematopoietic Regulator".

Cell Structure and Function, vol. 19, No. 6 (Dec. 1994), p. 543, XP 000564569, K. Takai et al, "Biological Fuction of HGF as a Hematopoietic Factor From Bone Marrow Stromal Cells".

*Primary Examiner*—Lorraine Spector
*Attorney, Agent, or Firm*—Griffin, Butler, Whisenhunt & Szipl, LLP

[57] ABSTRACT

Hepatocyte growth factor stimulates proliferation and differentiation of hematopoietic cells, most preferably burst-forming unit-erythroid cells. The hepatocyte growth factor may be obtained from cells transformed with human gene sequences coding therefor. Pharmaceutical compositions useful to induce the proliferation and differentiation of hematopoietic cells may contain hepatocyte growth factor as an active principle in admixture with a suitable carrier. The pharmaceutical compositions may additionally contain stem cell factor as an active principle.

3 Claims, 4 Drawing Sheets

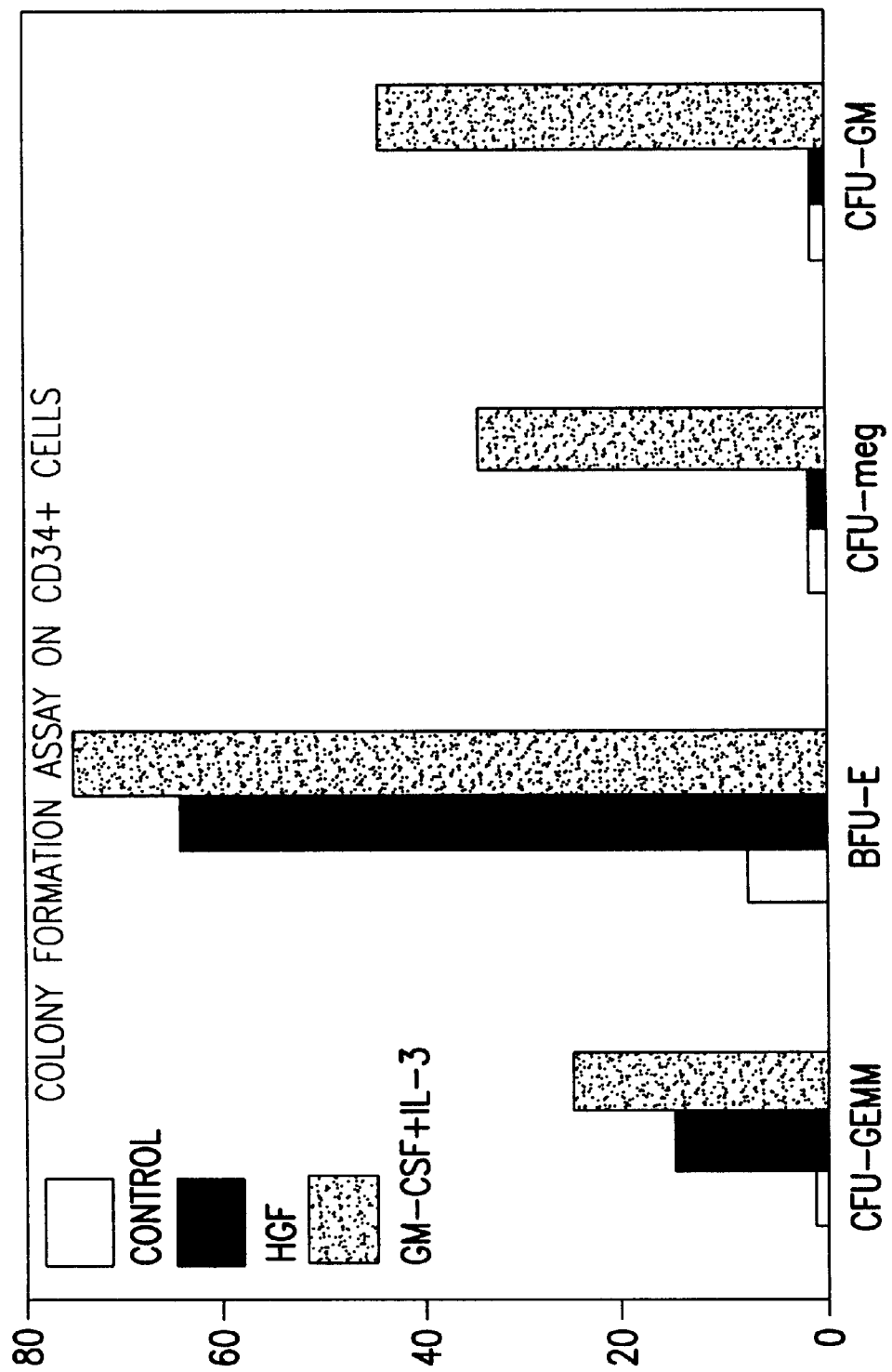

HEPATOCYTE GROWTH FACTOR—INDUCED PROLIFERATION AND DIFFERENTIATION OF ERYTHROID CELLS

This application is a 371 of PCT/EP95/04589.

FIELD OF THE INVENTION

The present invention relates to the use of the hepatocyte growth factor for the preparation of medicaments useful to induce proliferation and differentiation of hematopoietic cells, particularly multipotent and erythroid hematopoietic cell progenitors.

BACKGROUND OF THE INVENTION

Hepatocyte Growth Factor (HGF, the same abbreviation having also been used to define a completely different substance, i.e. hemopoiesis Growth factor) described by Nakamura et al., 1989, and by Hiyazawa et al., 1989), also known as Scatter Factor (Naldini et al., 1991a; Weidner et al., 1991), has the unique feature of combining mitogenic and motogenic activities on its target cells. HGF is mitogenic for hepatocytes (Michalopoulos, 1990) and other epithelial cells, such as kidney tubular epithelium, melanocytes and keratinocytes (Kan et al., 1991; Rubin et al., 1991; Halaban et al., 1992; Matsumoto et al., 1991). In these cells, HGF also promotes "scattering" (Stoker et al., 1987; Gherardi et al., 1989; Weidner et al., 1990, 1991; Naldini et al., 1991a) and matrix invasion (Weidner et al., 1990; Naldini et al., 1991a), and has chemotactic properties (Morimoto et al., 1991; Giordano et al., 1993). The factor stimulates extracellular matrix (ECM) degradation, by enhancing the synthesis of enzymes involved in ECM proteolysis (Pepper et al., 1992; Boccaccio et al., 1994). HGF acts as a morphogen in neuro-ectodermal development in vivo (Stern et al., 1990), and induces three-dimensional organization of epithelial cells in vitro (Montesano et al., 1991). The factor also promotes the progression of carcinoma cells toward malignant invasive phenotypes (Weidner et al., 1990).

The receptor for HGF is the tyrosine kinase encoded by the MET proto-oncogene (Naldini et al., 1991a, 1991b; Bottaro et al., 1991), a 190 kDa heterodimer of an extracellular 50 kDa α subunit, disulfide-linked to a transmembrane 145 kDa β subunit (Park et al., 1987; Giordano et al., 1989a) Both subunits derive from glycosylation and proteolytic cleavage of a 170 kDa single chain precursor (Giordano et al., 1989b).

The HGF receptor is expressed in adult epithelial tissues, including liver, intestine and kidney (Prat et al., 1991a; Di Renzo et al., 1991). It has been reported to be expressed in early stages of development of epithelial organs (Sonnenberg et al., 1993), and it is often overexpressed in epithelial cancer (Prat et al., 1991a; Di Renzo et al., 1991). We have shown that the receptor is also expressed in endothelial cells and that HGF is a potent angiogenic factor both in vitro and in vivo (Bussolino et al., 1992; Grant et al., 1993). The HGF receptor is also known to be expressed in some populations of blood cells, such as macrophages, but the meaning of such an expression, which is barely detectable in the absence of activation, has not been elucidated (Galini et al., 1993).

EP-A-0,492,614 discloses the use of HGF as a growth enhancer for epitheliocytes, whereas WO 93/08821 discloses the use of HGF for the prevention of the side-effects of chemotherapeuticals.

Now it has been found that the hepatocytes growth factor induces proliferation and differentiation of multipotent and erythroid hematopoietic progenitors.

Hematopoietic cell growth and differentiation is under the control of a complex network of cytokines, which act on their target cells via specific receptors (Metcalf, 1984; Clark and Kamen, 1987). Erythropoiesis is a complex process in which a specific genetic program is primed (commitment) and executed (maturation). Although much is known about maturation, most of the molecular events occurring during the commitment phase are still obscure. Growth and differentiation of erythroid precursor are regulated by humoral factors and by largely uncharacterized cell-cell interactions with bone marrow stroma, the so-called hematopoietic microenvironment. Erythropoietin has long been considered the major factor required for erythropoiesis (Koury and Bondurant, 1990), other factors being far less specific (IL-3, GM-CSF, TGF-β; Gasson, 1991; Miyajima et al., 1993; Sporn and Roberts, 1992). HGF represents a novel example of a humoral factor specifically active on erythropoiesis.

Recently, the synergism between HGF, IL-3 and GF, IL-3 and GM-CSF in promoting the growth of uncharacterized colonies from unfractionated murine bone marrow (Kmiecik et al., 1992) has been described. From said work, however, no conclusions about the effect of HGF alone could be deduced; moreover, the results obtained using bone marrow cell suspensions (including lymphocytes and monocytes-macrophages) could be ascribed to an indirect effect, mediated by the production of hematopoietic cytokines by accessory cells.

The synergism between HGF, IL-3 and GM-CSF, in fact, has not been confirmed by the authors of the present invention on isolated colonies of human hematopoietic cells.

SUMMARY OF THE INVENTION

It has been found that HGF stimulates erythroid and multipotent progenitors in vitro and that the HGF receptor is expressed in a sub-population of adult hematopoietic progenitors (CD34+). The obtained results, which are reported in detail in the examples, suggest that HGF is a paracrine mediator of stromal-hematopoietic cell interactions, both during embryogenesis and adult life. HGF may therefore be one of the molecules mediating developmental signals between microenvironment and hematopoietic progenitors.

As a consequence, HGF can be administered, according to the invention, to patients affected with pathologies in which the stimulation of hemopoiesis is desirable. Examples of such pathologies include primitive or secondary cytopenias of various origin. Moreover HGF can be used in all of the radio- or chemo-sensitive neoplastic pathologies in which the use of bone marrow autologous transplant could be suggested, also for the mobilization in the bloodstream of the hematopoietic precursors (scatter effect). Particularly, HGF can be used as mobilizer of the bone marrow precursors in the use of peripheral blood as a source of stem cells for bone marrow transplant. Moreover, HGF may be used, alone or in combination with other factors, for the ex vivo expansion of marrow hematopoietic precursors, in any clinical condition requiring it (Akabutu, J. J., Chan, J. R., Prog. Clin. Biol. Res. 389:399–404).

BRIEF DESCRIPTION OF THE DRAWINGS

FIG. 4 presents a colony formation assay on CD34+ cells.

DETAILED DESCRIPTION OF THE INVENTION

Figure 1C:
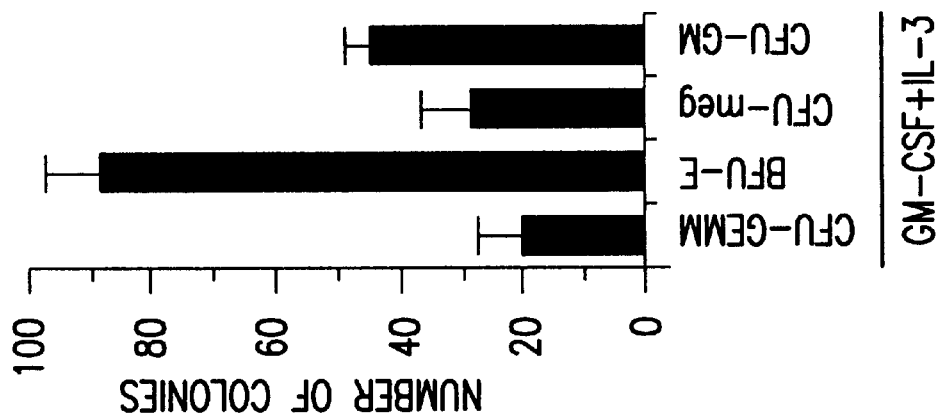
FIG. 1 graphically illustrates numbers of cell colonies obtained in the presence of specified substances.

For the envisaged therapeutical uses, HGF from different sources can be used, for example from animal or human organs or from prokaryotic or eukaryotic cells transformed with genes coding for HGF. By the term HGF, an activated form of HGF is obviously meant, such as described in Example 1 and 6. The use of human recombinant HGF is preferred, but the invention also applies to all the possible variants of HGF, including any deletion and/or substitution mutant forms. The hepatocyte growth factors will be formulated in dosage forms suitable to the administration of protein substances. The formulations of the invention therefore will be administered preferably by the parenteral route and they can be prepared using conventional techniques and excipients, as described for example in Remington's Pharmaceutical Sciences Handbook, Mack Pub. Co., N.Y., USA.

Anyhow, other administration routes already suggested for protein active principles, such as the nasal, sublingual, rectal and oral routes, cannot be excluded. For the latter, the active principle will suitably be protected from metabolic degradation making use of known techniques, for example the inclusion in liposome vesicles. The HGF dosage, according to the invention, may vary within wide ranges, for example from about 0.01 mg to about 10 mg of HGF, one or more times daily. The following examples further illustrate the invention.

EXAMPLE 1

Purification of human recombinant HGF from the Baculovirus expression system.

Full-length HGF cDNA was cloned from human liver mRNA and inserted into the Baculovirus transfer vector PVL1393 (Invitrogen, San Diego, Calif.). The recombinant vector was cotransfected with the Bsul-digested BacPak6 viral DNA (Clontech Laboratories, Palo Alto, Calif.) into Spodoptera frugiperda insect cells (Sf9) by the Lipofectin procedure (Gibco-BRL, Gaithersburg, Md.). Positive clones were identified and purified by dot-blot hybridization and plaque assay. The recombinant virus was used to infect Sf9 cells with dilutions of $10^{-1}$, $10^{-2}$, $10^{-3}$, $10^{-6}$. After one week, the infected cell extracts were blotted on a nylon filter and probed with radiolabelled full-length human HGF cDNA. The viruses containing the HGF cDNA gene were subsequently purified by plaque assay. Single viral clones were isolated and used for large scale infection of Sf9 cells.

The recombinant factor was purified by affinity chromatography on heparin (BioRad Laboratories, Hercules, Calif.), according to the procedure published by Weidner et al., 1990, with some modifications. Sf9 Spodoptera Frugiperda cells were grown at 27° C. in serum-free SF900 medium (Gibco Ltd, Scotland).

Exponentially growing cultures were infected by adding the viral stock in serumfree culture medium, and the cells were grown for 3 days. The culture medium was then collected and was incubated overnight in the presence of 3% foetal calf serum at 37° C., to ensure full activation of the precursor; it was then spun at 300×g for 15 min, to remove cellular debris, and cleared by centrifugation at 10,000×g for 1 h. The supernatant was buffered to pH=7.4 with TRIS, supplemented with a mixture of protease inhibitors (1 mM PMSF, 50 μg/ml leupeptin, 10 μg/ml aprotinin, 4 μg/ml pepstatin) and the detergent CHAPS to a final concentration of 0.2% w/v, filtered on a 0.45 μm pore Tuffryn membrane filter (Gelman Sciences, Ann Arbor, Mich.) by vacuum suction, cooled to 4° C. and applied to a 5 ml heparin-agarose column assembled in an FPLC apparatus in the cold room with a loading rate of 8 ml/h. The column was sequentially washed with 0.15 M NaCl, 50 mM Tris-HCl pH=7.4, 0.2% CHAPS and 0.5 M NaCl, 50 mM Tris-HCl pH=7.4, 0.2% CHAPS until the eluant absorbance returned to the baseline. Bound materials were eluted with a linear gradient from 0.5 M to 1.8M NaCl over 8 h in 50 mM Tris-HCl pH=7.4, CHAPS 0.2%, with a flow rate of 0.2 ml/min, and 2 ml fractions were collected. The starting material, the column breakthrough and washings, and the eluted fractions, were scored for the content of HGF by the MDCK scattering assay (Weidner et al., 1990; Naldini et al., 1992). The fractions containing the peak of HGF activity, eluting at approximately 1M NaCl, were pooled, concentrated with a diafiltration device with 30,000 molecular weight cut off (Amicon Div., Grace Industrial, Switzerland), checked for biological activity on MDCK cells, and purity by SDS-PAGE and protein stains, to give pure HGF with an average yield of the procedure of 150 μg from 700 ml of culture supernatant.

EXAMPLE 2

Production of human recombinant pro-HGF in insect cells. HGF cDNA was cloned from human liver mRNA (Naldini et al., 1991a) and inserted as a BamHI-EcoRI fragment into the baculovirus transfer vector PVL1393 (Invitrogen). The recombinant vector was co-transfected with the BsuI-digested BacPak6 viral DNA (Clontech) into Spodoptera frugiperda insect cells (Sf9), by the lipofectin procedure.

Positive viral clones isolated by dot-blot hybridization and plaque assay were used for large scale infection. HGF was obtained from culture supernatant of Sf9 infected cells 72 hours post-infection, by affinity chromatography on a heparin-Sepharose FPLC column (BioRad), eluted with a linear 0.5–1.8 M NaCl gradient. The unprocessed recombinant factor (pro˙ HGF) was detected by Comassie Blue staining as a band of 90 kDa in SDSPAGE. Protein concentration was estimated by Comassie Blue staining and comparison with a standard curve obtained with increasing amounts of bovine serum albumin.

EXAMPLE 3

Stimulation of erythroid and multipotent hematopoietic progenitors.

The effect of HGF on the growth and differentiation of hematopoietic progenitors was evaluated in colony formation assays. Heparinized samples of bone marrow, fetal umbilical cord blood and adult peripheral blood, obtained from volunteers, were diluted with an equal volume of Phosphate Buffered Saline (PBS), and separated by Ficoll-Hypaque 1077 SD (Pharmacia) density gradient centrifugation at 550 g for 30 minutes. Light-density mononuclear cells (LD-MC) were collected, washed twice in PBS and resuspended in Iscove Modified Dulbecco's Medium (IMDM) (Gibco) supplemented with 5% Fetal Calf Serum (FCS). Mononuclear adherent cells were then removed by a two steps incubation of 30 minutes each in plastic flasks at 37° C.

Mononuclear non-adherent cells (MNAC) were incubated with neuraminidase-treated sheep erythrocytes for 15 minutes at 37° C., centrifuged and incubated for 45 minutes at 4° C. T-lymphocyte-depleted MNAC were separated by Ficoll-Hypaque 1077 SD (Pharmacia) density gradient centrifugation.

T-lymphocyte-depleted MNAC were then incubated for 45 minutes at 4° C. with the following antibodies: anti-CD3, anti-CD4, anti-CD8, antiCD11, anti-CD19, anti-CD57; most of the remaining B- and T- lymphocytes, monocytes and granulocytes were thus removed by incubation for 45 min. at 4° C. with immunomagnetic beads coated with anti-mouse IgG (M-450 Dynabeads, Dynal), subsequently collected by a magnet (MPC-1 Dynabeads, Dynal).

A positive selection of the CD34+ cells was then performed: cells were incubated with an antibody anti-CD34 (My-10; Technogenetics) for 45 minutes at 4° C., then for 45 minutes at 4° C. with immunomagnetic beads coated with anti-mouse IgG; a 4:1 beads/cell ratio was found to provide the best recovery. CD34+ cells bound to the beads were then collected by a magnet and resuspended in IMDM supplemented with 10% FCS. An overnight incubation at 37° C. was then performed; to allow CD34+ cells detachment, the beads were subjected to shearing forces by repeated flushing through a Pasteur pipette. Further details about the negative/positive double selection procedure used have been published previously (Bagnara et al., 1991). The recovered cells were morphologically unidentifiable blast elements on May-Grunwald-Giemsa staining, slightly contaminated by pro-myelocytes. Flow cytometry analysis indicated that the percentage of CD34+ cells in the selected cell preparations varied between a minimum of 30% (when the starting material was bone marrow) and a maximum of 50% (when the starting material was peripheral blood). Contamination by CD4+, CD2+, CD16+ or CD19+ cells was constantly below 1%.

The colony assay for erythroid Burst-Forming Units and for multipotent Colony-Forming Units (CFU-GEMM) was performed according to Iscove et al., 1974. Cord blood, bone marrow or peripheral blood CD34+ cells were plated in 24-well cell culture clusters (Costar), at a density of $2.5 \times 10^3$ cells/well, in a medium containing IMDM, 30% FCS, $2 \times 10^{-4}$ M hemin, $5 \times 10^{-5}$ β-mercaptoethanol and 0.9% methylcellulose. The cells were stimulated with the following growth factors alone or in combination: Epo 2 ng/ml, IL-3 2 ng/ml, GH-CSF 50 ng/ml, SCF 20 ng/ml, pro-HGF 2, 10 or 40 ng/ml. Colonies scored positive only when dark-red and containing more than four aggregates.

The assay for the 14-day Granulo-Monocyte Colony-Forming Units (CFU-GM) was performed as previously described (Iscove et al., 1971). Cord blood, bone marrow or peripheral blood CD34+ cells were plated in 24-well cell culture clusters (Costar), at a density of $2.5 \times 10^3$ cells/well, in a medium containing IMDM, 20% FCS, 0.3% Noble agar (Difco) and the following growth factors alone or in combination: IL-3 2 ng/ml, GM-CSF 50 ng/ml, SCF 20 ng/ml, pro-HGF 2, 10 or 40 ng/ml.

For the Megakaryocyte Colony-Forming Unit (CFU-meg) assay, plasma clot assay was performed according to Vainchenker et al., 1979. Cord blood, bone marrow or peripheral blood CD34+ cells were plated in 24-well cell culture clusters (Costar), at a density of $2.5 \times 10^3$ cells/well, in a medium containing IMDM, 20 mg/ml L-Asparagine (Sigma), 3.4 mg/ml $CaCl_2$, 10% bovine plasma citrated (GIBCO), 1% detoxified bovine serum albumin (BSA, fraction V Chon) (Sigma), 10% of heat-inactivated human AB serum and the following growth factors alone or in combination: IL-3 2 ng/ml, GM-CSF 50 ng/ml, SCF 20 ng/ml, pro-HGF 2, 10 or 40 ng/ml. After 12 days of incubation, the plasma clot was fixed in situ with methanol-acetone 1:3. for 20 minutes, washed with PBS and air dried. Fixed plates were stored at −20° C. until immunofluorescence staining was performed; CFU-meg colonies were scored as aggregates of 3–100 cells intensively fluorescent to monoclonal antibody CD41 (Immunotech) directed against the IIb/IIIa glycoprotein complex. Binding was shown by fluorescein-conjugated goat anti-mouse Ig (Becton Dickinson).

Figure 1B:
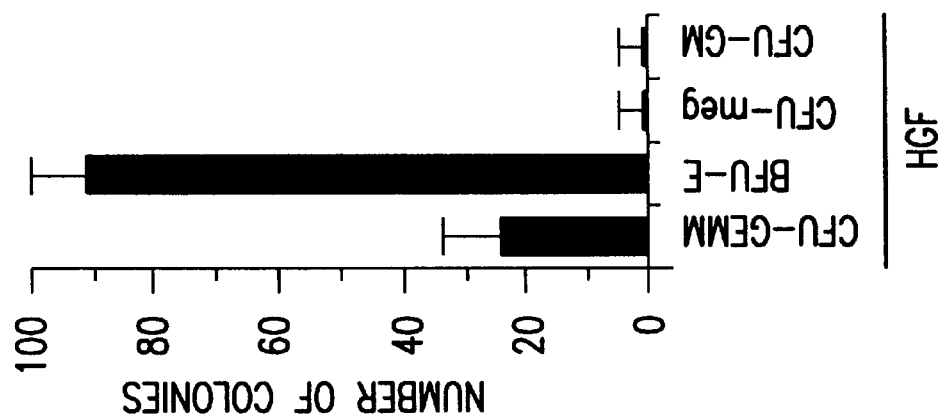
Figure 1A:
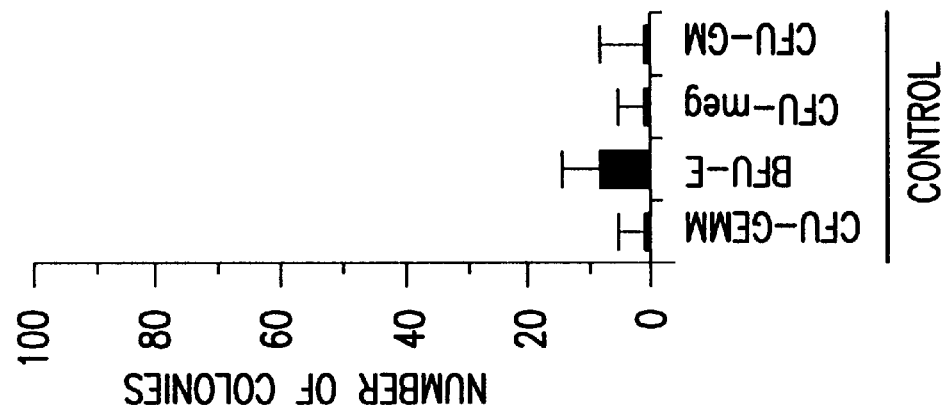
Figure 2A:
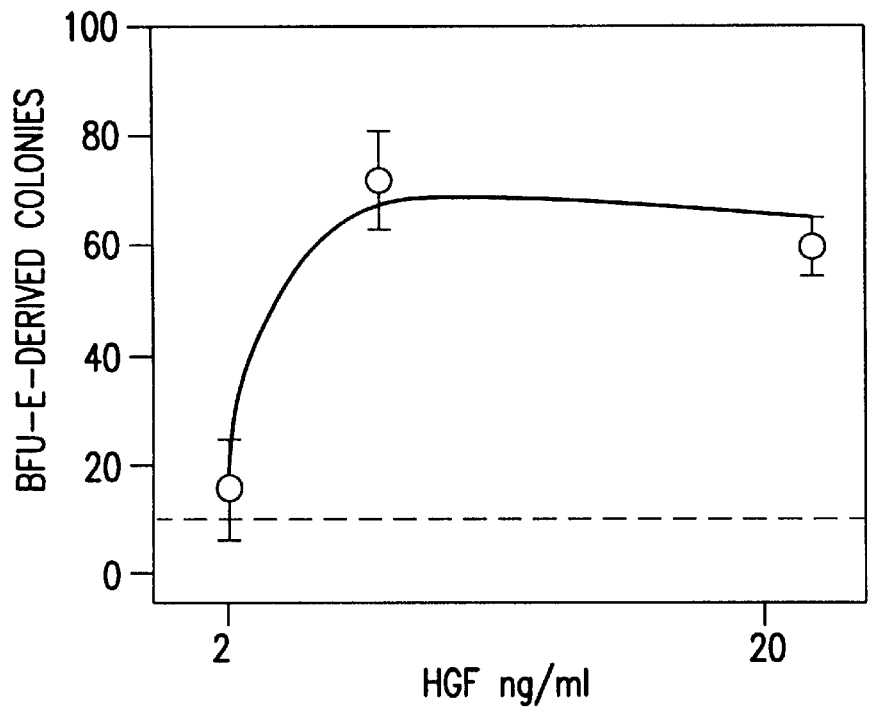
FIG. 2 graphically compares numbers of BFU-E and CFU-GEMM derived colonies.
Figure 2B:
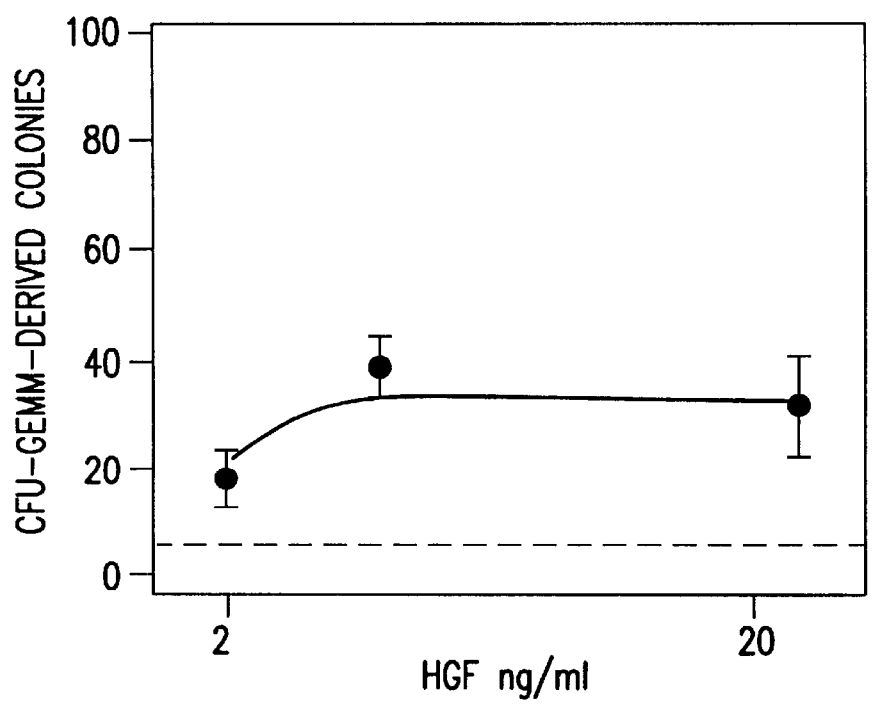

The results are schematized in FIGS. 1 and 2, and they show that, in the presence of standard concentrations of erythropoietin (2 ng/ml), HGF dramatically increased the number of colonies derived from the BFU-E precursors (FIG. 1). HGF also stimulated the growth of colonies derived from multipotent CFU-GEMM progenitors. The number of colonies was comparable to that obtained by combining known hemopoietic factors such as GM-CSF and Interleukin-3 (Gasson, 1991; Miyajima et al., 1993). It should be noted, however, that the HGF effect was restricted to the stimulation of CFU-GEMM and BFU-E.

Neither granulo-monocytic nor megakaryocytic colonies were ever observed in response to HGF.

The response to HGF was dose-dependent and could be observed at concentrations of HGF as low as 5 pM both in erythroid and multipotent colonies (FIG. 2).

The HGF action was also studied on CD34+ foetal hematopoietic progenitors, enriched from human umbilical cords blood. It is known that this population contains a percentage of primitive stem cells higher than the population purified from adult bone marrow or peripheral blood (Broxmeyer et al., 1992; Lu et al., 1993). As observed in the case of adult hematopoietic progenitors, HGF stimulated both BFU-E and CFU-GEMM derived colonies.

Figure 3C:
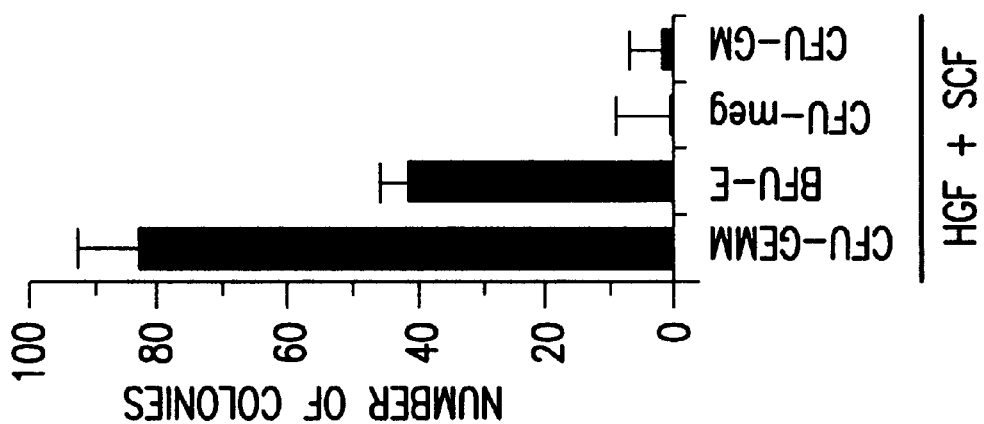
FIG. 3 graphically illustrates numbers of cell colonies obtained In the presence of stem cell factor.
Figure 3B:
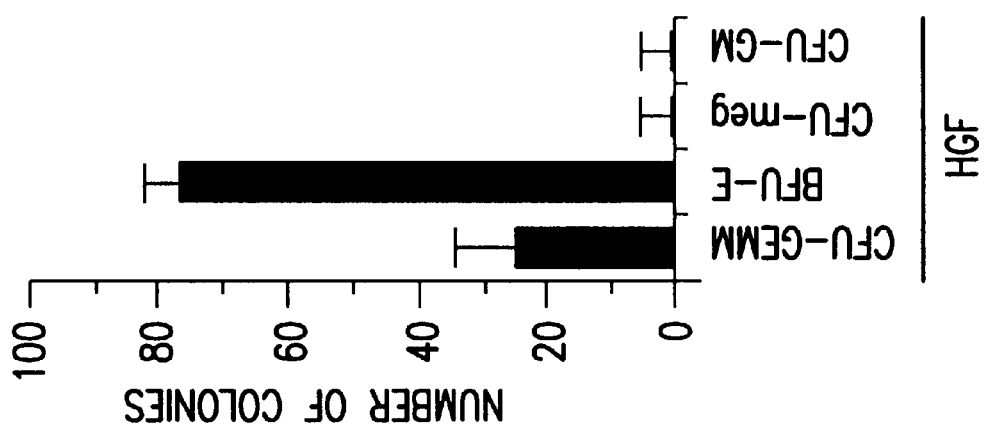
Figure 3A:
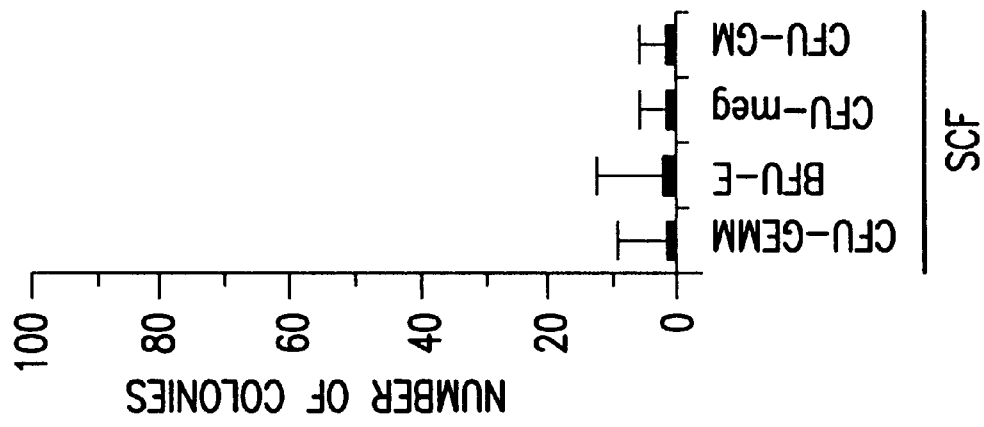

In the presence of both HGF and Stem Cell Factor (SCF), a significant increase in the number of CFU-GEMM-derived colonies was observed (FIG. 3). In this case, fewer erythroid colonies could be seen compared to those developed in the cultures stimulated by HGF alone. This suggests that the combination of HGF and SCF preferentially affects proliferation of multipotent progenitors.

The erythroid colonies grown in the presence of both growth factors were extremely large and showed a high hemoglobin content. The size of CFU-GEMM derived colonies grown in these conditions was also increased and, within each colony, the erythroid lineage was predominant.

In these assays HGF did not synergize with GM-CSF and Interleukin-3, either tested individually or in combination.

EXAMPLE 4

Expression of the HGF receptor in a subpopulation of adult hematopoietic progenitors (CD34+).

The presence of HGF receptor at the surface of hematopietic progenitors was studied by flow cytometry analysis of bone marrow and peripheral blood mononuclear cells. Monoclonal antibodies directed against extracellular epitopes of the HGF receptor β chain were used. A small but clearly identifiable subpopulation of bone marrow cells stained positive for the HGF receptor (Table).

|   |   | Phenotype | Positive Cells % |
|---|---|---|---|
| A. | Unfractionated bone marrow | HGF-R+ | 0.6 ± 0.1 |
|   |   | HGF-R+/CD34+ | 0.3 ± 0.05 |
|   |   | HGF-R+/CD34− | 0.3 ± 0.1 |
|   |   | HGF-R+/SCF-R+ | 0.2 ± 0.1 |
|   |   | HGF-R+/SCF-R− | 0.4 ± 0.1 |
| B. | CFU-GEMM-derived colonies | HGF-R+ | 15.3 ± 1.5 |
| C. | BFU-E-derived colonies | HGF-R+ | 9.7 ± 1.2 |

About half of the cells expressing the HGF receptor also co-expressed the CD34 marker and could thus be identified as hematopoietic-progenitors.

As described above, HGF synergized with the SCF in stimulating the growth and differentiation of CFU-GEMM derived colonies. In line with this observation, a subpopulation of cells co-expressing the HGF and the SCF receptors was identified using a monoclonal antibody against extracellular epitopes of the SCF receptor.

Similar results were obtained by flow cytometry analysis of CD34+ progenitors circulating in the peripheral blood.

Flow cytometry analysis with anti-HGF-receptor antibodies was also performed on cells harvested from the colonies developed in vitro in response to HGF. The Table shows that HGF-receptor positive cells were present.

EXAMPLE 5

Expression of HGF and its receptor during the embryonal development of hematopoietic cells.

The expression of the HGF receptor was studied in embryonal hematopoietic cells by in situ hybridization of histological sections of mouse embryos. Using an antisense MET probe, the HGF receptor mRNA could be clearly detected in megaloblastic cells located within the cavity of the developing heart and aorta from 10–10.5 days post coitum. Specific mRNA could be detected in the hepato/biliary primordium, which at this stage contains hemopoietic precursors. In this developing organ erythroid islands showed a higher levels of HGF receptor mRNA, compared with the level of expression observed in the surrounding hepatocytes. From 11 days post coitum the hematopoietic embryonal liver also expressed HGF mRNA.

EXAMPLE 6

In order to prove the mobilization of the bone marrow hemopoietic precursors at the peripheral blood, the murine model has been used. Balb/C mice were treated subcutaneously for 4 days with HGF at varied concentrations or with control preparations. At the end of the treatment, mice were killed, the circulating leukocytes were counted and hemopoietic colonies from peripheral blood were cultured. In HGF-treated mice, contrary to the untreated controls, an about 60% increase in circulating leukocytes was observed as well as an increase in the colonies obtainable from peripheral blood. This phenomenon has an intensity comparable with that of G-CSF, already described and used to mobilize bone marrow hematopoietic precursors (Janssen, W. E., et al., Prog. Clin. Biol. Res. 389:429–39).

EXAMPLE 7

Using in the colony formation assay on CD34$^+$ cells of Example 3 equimolecular amounts of activated HGF, obtained according to Example 1, instead of pro-HGF, statistically similar results have been obtained in the colonies count as shown in the enclosed FIG. 4.

REFERENCES

1. Bagnara, G. P., G. Zauli, L. Vitale, P. Rosito, V. Vecchi, G. Paolucci, G. C. Avanzi, U. Ramenghi, F. Timeus, and V. Gabutti, 1991. In vitro growth and regulation of bone marrow enriched CD34+ hematopoietic progenitors in Diamond-Blackfan anemia. Blood. 78; 2203–2210.
2. Boccaccio, C., G. Gaudino, G. Gambarotta, F. Galimi, and P. M. Comoglio. 1994. Hepatocyte Growth Factor receptor expression is inducible and is part of the delayed-early response to HGF. J. Biol. Chem. In press.
3. Bottaro, D. P., J. S. Rubin, D. L. Faletto, A. M. L. Chan, T. E. Kmiecick, G. F. Vande Woude, and S. A. Aaronson. 1991. Identification of the Hepatocyte Growth Factor receptor as the c-met proto-oncogene. Science. 251: 802–804.
4. Broxmeyer, H. E., Hangoc, G., Cooper, S., Riberio, C., Greaves, V., Yoder, M., Wagner, J., Vadhan-Raj, S., Benninger, L., Rubinstein, P., and Randolph Brown E. 1992. Growth characteristics and expansion of human umbilical cord blood and estimation of its potential for transplantation in adults. Proc. Natl. Sci. (USA) 89: 4109–4113.
5. Broxmeyer, E. H., R. Maze, K. Miyazawa, C. Carow, P. c. Hendrie, S. Cooper, G. Hangoc, S. Vadham-Raj, and L. Lu. 1992. The c-kit receptor ands its ligand, Steel, as regulators of hemopoiesis. Cancer Cells. 3: 480–487.
6. Bussolino, F., M. F. Di Renzo, M. Ziche, E. Bocchietto, M. Oliviero, L. Naldini, G. Gaudino, L. Tamagnone, A. Coffer, and P. M. Comoglio. 1992. Hepatocyte growth factor is a potent angiogenic factor which stimulates endothelial cell motility and growth. J. Cell. Biol. 119: 629–641.
7. Clark, S. C., and R. Kamen. 1987. The human hematopoietic colony-stimulating factors. Science. 236: 1229–1237.
8. Di Renzo, M. F., R. P. Narsimhan, M. Olivero, S. Bretti, S. Giordano, E. Medico, P. Gaglia, P. Zara, and P. M. Comoglio. 1991. Expression of the Met/HGF receptor in normal and neoplastic human tissues. Oncogene. 6: 1997–2003.
9. Galimi, F., Brizzi, M. F., Comoglio, P. M., 1993. The hepatocyte growth factor and its receptor. Stem cells II Suppl 2, 22–30.
10. Gasson, J. 1991. Molecular physiology of granulocyte-macrophage colony-stimulating factor. Blood. 77: 1131–1145.
11. Gherardi, E., J. Gray, M. Stoker, M. Perryman, and A. Furlong. 1989. Purification of scatter factor, a fibroblast basic protein that modulates epithelial interactions and movement. Proc. Natl. Acad. Sci. USA. 86: 5844–5848.
12. Giordano, S., C. Ponzetto, M. F. Di Renzo, C. S., Cooper, and P. M. Comoglio. 1989a. Tyrosine kinase receptor indistinguishable from the c-met protein. Nature. 339: 155–156.
13. Giordano, S., M. F. Di Renzo, R. Narshimhan, C. S. Cooper, C. Rosa, and P. M. Comoglio. 1989b. Biosynthesis of the protein encoded by the c-met proto-oncogene. Oncogene. 4: 1383–1388.
14. Giordano, S., Z. Zhen, E. Medico, G. Gaudino, F. Galimi, and P:M: Comoglio. 1993. Transfer of the motogenic and invasive response to scatter factor/hepatocyte growth factor by transfection of the human c-MET pro-tooncogene. Prac. Natl. Acad. Sci. USA. 90: 649–653.
15. Grant, D. S., H. K. Kleinman, I. D. Goldberg, M. Bhargava, B. J. Nickoloff, J. L. Kinsella, P. J. Polverini, and E. M. Rosen. 1993. Scatter Factor induces blood vessel formation in vivo. Proc. Natl. Acad. Sci. USA. 90: 1937–1941.
16. Halaban, R., J. F. Rubin, Y. Fusanaka, M. Cobb, T. Boulton, D. Faletto, E. Rosen, A. Chan, K. Yoko, W. White, C. Cook, and G. Moellmann. 1992. Met and Hepatocyte Growth Factor/Scatter Factor signal transduction in normal melanocytes and melanoma cells. Oncogene. 7: 2195–2206.
17. Iscove, N. N., S. Senn, J. E Till, and E. A. McCulloch. 1971. Colony formation by normal and leukemic human marrow cells in culture: effect of conditioned medium from human leukocytes. Blood. 37: 1–5.
18. Iscove, N. N., F. Sieber, and H. Winteralter. 1974. Erythroid colony formation in cultures of mouse and human bone maroow: analysis of the requirement for erythropoietin by gel filtration and affinity chromatography on agarose-concanavalin A. J. Cell. Physiol. 83: 309–320.

19. Kan, M., G. H. Zhang, R. Zarnegar, G. Michalopoulos, Y. Myoken, W. L. Mckeehan, and J. L. Stevens. 1991. Hepatocyte Growth Factor/Hepatopoietin A stimulates the growth of rad kidney proximal tubule epithelial cells (RPTE), rat nonparenchymal liver cells, human melanoma cells, mouse keratinocytes and stimulates anchorage-independent growth of SV40-transfomed RPTE. Biochem. Biophys. Res. Commun. 174: 331–331.

20. Kmiecik, T. E., I. R. Kelleer, E. Rosen, and G. F. Vande Woude. 1992. Hepatocyte Growth Factor is a synergistic factor for the growth of hematopoietic progenitor cells. Blood. 16: 2454–2457.

21. Koury, M. J., and M. C. Bondurant. 1990. Erythropoietin retards DNA breakdown and prevents programmed death in erythroid progenitor cells. Science. 248: 378–381.

22. Lu, L., M. Xiao, R. N. Shen, S. Grisby, and H. E. Broxmeyer. 1993. Enrichment, characterization and responsiveness of single primitive CD34+ human umbilical cord blood hematopoietic progenitors with high proliferative and replating potential. Blood. 81: 41–48.

23. Matsumoto, K., Hashimoto, K. Yoshikaua, and T. Nakamura. 1991. Marked stimulation of growth and motility of human keratinocytes by Hepatocyte Growth Factor. Exp. Cell. Res. 196: 114–120.

24. Metcalf, D. 1984. The Hemopoietic Colony Stimulating Factors. Elsevier, Amsterdam.

25. Metcalf, D. 1987. The molecular control of cell division, differentiation, commitment and maturation in hemopoietic cells. Nature. 339: 27–30.

26. Michalopoulos, G. K. 1990. Liver regeneration: molecular mechanisms of growth control. FASEB J. 4: 176–187.

27. Miyajima, A., A. L. Mui, T. Ogorochi, and K. Sakamaki. 1993. Receptors for granulocyte-macrophage colony-stimulating factor, interleukin-3 and interleukin-5. Blood. 82: 1960–1974.

28. Miyazawa, K., H. Tsubouchi, D. Naka, K. Takahashi, H. Okigaki, N. Arakaki, H. Nakayama, S. Hirono, O. Sakiyama, K. Takahashi, E. Godha, Y. Daikuhara, and N. Kitamara. 1989. Molecular Cloning and Sequence Analysis of cDNA for Human Hepatocyte Growth Factor. Biochem. Biophys. Res. Commun. 163: 967–973.

29. Montesano, R., K. Matsumoto, T. Nakamura and L. Orci. 1991. Identification of a Fibroblast-Derived Epithelial Morphogen as Hepatocyte Growth Factor. Cell. 67: 901–908.

30. Nakamura, T., T. Nishizawa, M. Hagiya, T. Seki, M. Shimonishi, A. Sugimura, K. Tashiro, and S. Shimizu. 1989. Molecular cloning and expression of human Hepatocyte Growth Factor. Nature. 342: 440–443.

31. Naldini, L., M. Weidner, E. Vigna, G. Gaudino, A. Bardelli, C. Ponzetto, R. Narshimhan, G. Hartmann, R. Zarnegar, G. Michalopoulos, W. Birchmeier, and P. M. Comoglio. 1991a. Scatter Factor and Hepatocyte Growth Factor are indistinguishable ligands for the Met receptor. EMBO J. 10: 2867–2878.

32. Naldini, L., E. Vigna, R. P. Narshiman, G. Gaudino, R. Zarnegar, G. Michalopoulos, and P. M. Comoglio. 1991b. Hepatocyte Growth Factor (HGF) stimulates the tyrosine kinase activity of the receptor encoded by the proto-oncogene c-MET. Oncogene. 6: 501–504.

33. Park, M., M. Dean, K. Kaul, M. J. Braun, M. A. Gonda, and G. F. Vande Woude. 1987. Sequence of MET proto oncogene cDNA has features characteristic of the tyrosine kinase family of growth-factor receptors. Proc. Natl. Acad. Sci. USA. 84: 6379–6383.

34. Pepper, M. S., K. Matsumoto, T. Nakamura, L. Orci, and R. Montesano. 1992. Hepatocyte growth factor increases urokinase-type plasminogen activator ($\mu$-PA) and $\mu$-PA receptor expression in Madin-Darby canine kidney epithelial cells. J. Biol. Chem. 267: 20493–20496.

35. Prat, M., R. P. Narsimhan, T. Crepaldi, M. R. Nicotra, P. G. Natali, and P. M. Comoglio. 1991a. The receptor encoded by the human c-MET oncogene is expressed in hepatocytes, epithelial cells and solid tumors. Int. J. cancer. 49: 323–328.

36. Rubin, J. S., A. M. L. Chan, D. P. Bottaro, W. H. Burgess, W. G. Taylor, a.C. Cech, D. W. Hirschfield, J. Wong, T. Hiki, P. W. Finch, and S. A. Aaronson. 1991. A broad-spectrum human lung fibroblast-derived mitogen is a variant of Hepatocyte Growth Factor. Proc. Natl. Acad. Sci. USA. 88: 415–419.

37. Sonnenberg E., D. Meyer, K. M. Weidner, and C. Birchmeier. 1993. Scatter Factor/Hepatocyte Growth Factor and its receptor, the c-Met tyrosine kinase, can mediate a signal exchange beyween mesenchyme and epithelia during mouse development. J. Cell. Biol. 123: 223–235.

38. Sporn, M. B., and A. B. Roberts. 1992. Transforming growth factor-$\beta$: recent progress and new challenges. J. Cell. Biol. 119: 1017–1021.

39. Stern, C. D., G. W. Ireland, S. E. Herrick, E. Gherardi, J. Gray, M. Perryman, and M. Stoker. 1990. Epithelial scatter factor, and M. Stoker. 1990. Epithelial scatter factor, and M. Stoker. 1990. Epithelial scatter factor and development of the chick embryonic axis. 110: 1271–1284.

40. Stoker, M., E. Gherardi, M. Perryman, and J. Gray. 1987. Scatter factor is a fibroblast-derived modulator of epithelial cell mobility. Nature. 327: 239–242.

41. Vainchenker, W., J. Bouquet, J. Guichard, and J. Breton-Gorius. 1979. Megakaryocyte colony formation from human bone marrow precursors. Blood 59: 940–945.

42. Weidner, K. M., J. Behrens, J. Vandekerckove, and W. Birchmeier. 1990. Scatter Factor: molecular characteristics and effect on the invasiveness of epithelial cells. J. Cell. Biol. 11: 2097–2108.

43. Weidner, K. M., N. Arakaki, J. Vandekerchove, S. Weingart, G. Hartmann, H. Rieder, C. Fonatsch, H. Tsubouchi, T. Hishida, Y. Daikuhara, and W. Birchmeier. 1991. Evidence for the identity of human Scatter Factor and Hepatocyte Growth Factor. Proc. Natl. Acad. Sci. USA. 88: 7001–7005.

I claim:

1. A method of stimulating proliferation and differentiation of burst-forming unit-erythroid (BFU-E) cells in vitro which comprises treating said cells with an effective amount of hepatocyte growth factor (HGF).

2. The method according to claim 1, wherein the hepatocyte growth factor is obtained from cells transformed with a human gene sequence coding for HGF.

3. The method of claim 1, wherein HGF is used in a concentration of at least 5 pM.

* * * * *